United States Patent [19]

Kurz

[11] 4,348,177

[45] Sep. 7, 1982

[54] PULSATING ORTHODONTIC APPLIANCE

[76] Inventor: Craven H. Kurz, No. 6 North Star, Apt. 106, Marina del Rey, Calif. 90291

[21] Appl. No.: 287,493

[22] Filed: Jul. 27, 1981

[51] Int. Cl.³ .............................................. A61C 7/00
[52] U.S. Cl. ................................................... 433/5
[58] Field of Search .......................................... 433/5

[56] References Cited

U.S. PATENT DOCUMENTS 4,123,844 11/1978 Kurz ...................................... 433/5
4,244,688 1/1981 Kurz ...................................... 433/5

Primary Examiner—Robert Peshock
Attorney, Agent, or Firm—Keith D. Beecher

[57] ABSTRACT

An orthodontic appliance for treating the maxillary molars, and which includes a cervical extra oral headgear, is provided. The appliance applies a pulsating force to the molars being treated, rather than a continuous force as is the case with the prior art devices. The invention is predicated on the concept that the pulsational effect of the tooth on the adjacent periodontal membrane and bone tends to loosen their fibrous structure, and helps the tooth to find the path of least resistance through the bone. The pulsating force in the appliance of the present invention is provided by a resilient elastic pad which is mounted on the oclusal surface of one of the maxillary molars, and which forces a liquid into a reservoir mounted on the headgear so as to produce an intermittent pulsation in the pressure delivered by the headgear to the molars being treated.

4 Claims, 3 Drawing Figures

U.S. Patent  Sep. 7, 1982  4,348,177
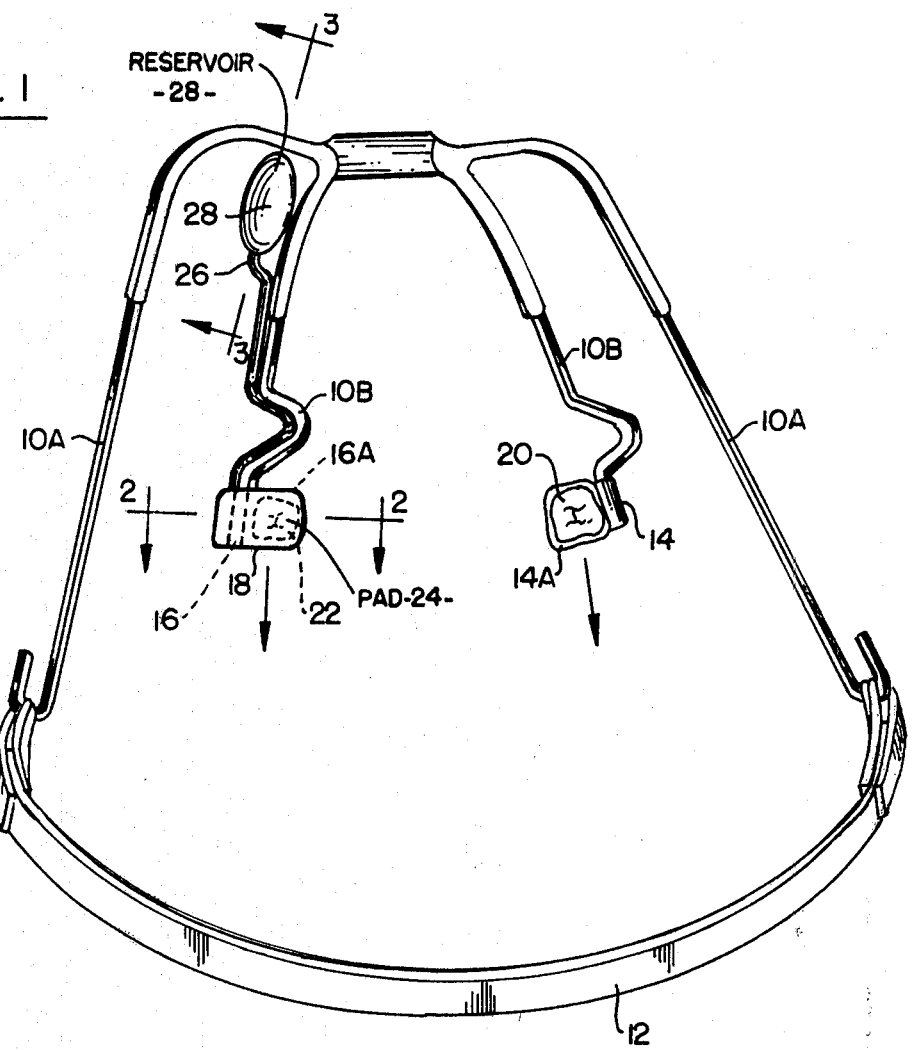
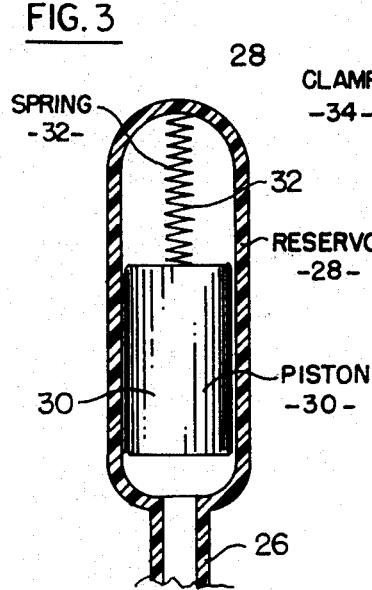
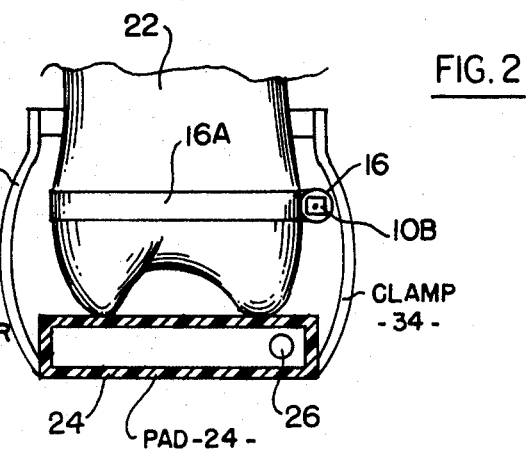

PULSATING ORTHODONTIC APPLIANCE

BACKGROUND OF THE INVENTION

The conventional method of orthodontic tooth movement, as practiced in the prior art, has been one of constant pressure applied to the tooth in order to move it through the adjacent bone. Constant pressure applied to the periodontal membrane by traditional orthodontic appliances causes the periodontal fibers to become cell free which results in standstill of the tooth. Compression of tissue results in reduced blood supply and tissue necrosis, and the tooth will not move again until the bone subjacent to the hyalinized tissue has been eliminated by undermining resorption. Generally, it is essentially the magnitude of the force which will determine the duration of the hyalinization. Moreover, the strong forces produce a wide hyalinization area of long duration. A discussion of this phenomenon may be found on Pages 76 and 97 of Current Orthodontic Concepts and Techniques, T. M. Graber, Editor, published by W. B. Saunders & Co. 1969.

When a tooth is tipped by a continuous force exerted on it by a usual prior art orthodontic appliance, the periodontal membrane is compressed in a circumscribed area situated close to the alveolar crest. This area becomes cell free and the blood vessels are occluded, and osteoclastic activity is reduced to a minimum. A description of this occurrence may be found, for example, at Page 497 of Orthodontic Principles and Practice by Graber, 2d Edition, published by Saunders & Co., 1967. If the pressurized area of periodontal membrane during the movement of a tooth by an orthodontic device is not compressed by strong forces, then the formation of osteoclasts, the cells responsible for resorption of bone, will be enhanced. The flow of blood to the area will not be restricted, and consequently osteoclastic activity will become more vigorous and bone resorption will be increased.

U.S. Pat. No. 4,229,165, which issued to the present inventor, discloses an orthodontic appliance which introduces pressure impulses to the tooth being treated, rather than a continuous force. With every pressure impulse from the appliance, the tissue pressure in the periodontal membrane and adjacent bone tissue is increased. When pressure is relaxed, the tissue fluid in the periodontal membrane and adjacent bone tissue is reduced. This fluctuation from high pressure to low pressure in the periodontal and adjacent tissue results in a pump-like action that sucks blood and tissue fluid into the area, and which then expels fluid from the area, for each cycle of operation. This serves to increase cellular action around the moving tooth, giving rise to more osteoclasts for bone resorption and more osteoblasts for bone aposition.

The active exchange of fluid during the pulsating operation of the appliance described in the patent helps to carry the by-products of bone resorption out of the resorption area. The pulsating tooth movement applied by the appliance is psychological and dynamic in nature, rather than pathological. Because the pulsation pressure exerted by the appliance does not result in areas of hyalinization and necrosis thereis no root resorption or horizontal bone lotion. The pump-like action of the tooth being pulsated by the appliance described in the patent is the same on the tension side of the tooth as on the compression side, but opposite in the timing cycle. On the tension side of the tooth, the increased blood supply results in increased cellular activity.

As a result, the use of the pulsating orthodontic appliance of the patent results in faster movement of the tooth, reduction of root resorption during orthodontic movement, reduction of horizontal bone loss during bone reconstruction, reduced discomfort from heavy orthodontic pressures, and reduction in tooth extrusion from their bony sockets when pressurized. The total effect resulting from the use of the orthodontic appliance of the patent is that tooth movementis of a psychological nature causing little or no irreversible results to the tooth or horizontal level, and expediting the travel of the tooth along its path through the adjacent bone so as to obtain the most rapid orthodontic movement in a painless environment.

The appliance of the present invention uses an extra oral headgear to achieve the pulsation effect, and it is even more effective than the appliance described in the patent. The source of the pulsations in the appliance of the invention is in the natural masticating action of the patient's lower jaw, and the pressure pulse delivered by the headgear occurs when there is no occlusal pressure on the teeth and is, therefore, more effective. This is because, at that moment there is no occlusion that would impede distalization of the molars being treated. Moreover, the pressure pulse from the occlusal pad is directed in a manner to prevent the headgear from causing extensions of the maxillary molars.

As described briefly above, in the practice of the present invention, a resilient elastic pad is mounted on the occlusal surface of one of the maxillary molars, and each time the lower molars close on the upper molars this pad is squeezed, and liquid in the pad is translated under pressure into a resilient elastic reservoir which is attached to the headgear. The appliance may be unilateral in operation, or bilateral, depending upon the particular needs of the patient.

The pressure that builds up in the anterior reservoir presses back on the molars being treated when the lower molar releases the pressure of the occlusal pad. This provides an intermittent pulsation of the pressure delivered by the headgear. As noted above, the source of the pulsation is in the natural masticating action of the lower jaw, and the pulsation pressure that is delivered to the molars being treated occurs when there is no occlusal pressure on the molars and consequently is most effective, since it occurs at the moment when there is no resistance from the occlusion that would otherwise impede movement of the molars. The vertical pressure from the occlusal pad also prevents the headgear from causing extension of the molars being treated.

Every time a person swallows, his teeth come together to result in the pulsating pressure. since a preson swallows over five thousand times daily, adequate pulsation frequently is provided.

BRIEF DESCRIPTION OF THE DRAWINGS

FIG. 1 is a top plan view of one embodiment of the appliance of the present invention, including a cervical extra oral headgear, which is illustrated as attached to both the maxillary molars;

FIG. 2 is a view of a portion of the appliance of FIG. 1, taken essentially along the line 2—2 of FIG. 1; and FIG. 3 is a sectional view of a reservoir which is included in the appliance of FIG. 1, taken essentially along the line 3—3 of FIG. 1, and illustrating certain internal components of the reservoir.

DETAILED DESCRIPTION OF THE ILLUSTRATED EMBODIMENT

The appliance shown in FIG. 1 includes an extra oral cervical head gear 10 having an outer bow 10A and an inner bow 10B. A resilient band 12 is attached to the ends of the outer bow 10A, and the band extends around the neck of the wearer; and the respective ends of the inner bow 10B are attached to the maxillary molars 20 and 22 of the patient. The inner end of bow 10B, for example, extends into a tube 14 which is adhesively attached to molar 20, or which is attached to the molar by a band 14A. Likewise, the end of the inner bow 10B extends into a tube 16 which is adhesively attached to molar 22, or which is attached to the molar by means of a band 16A.

A resilient elastic pad 24 is mounted on the occlusal surface of maxillary molar 22 by means, for example, of appropriate clamps 30. The clamps are attached to the sides of the tooth, and the pad may be removed from the clamps, and from the occlusal surface of the molar, whenever the patient takes off the headgear. Then, the pad may be remounted on the molar when the patient again puts on the headgear. The pad 24 is filled with an appropriate liquid, and is coupled to a reservoir 28 through a tube 26. The reservoir, as shown, is mounted on the headgear. The reservoir is made of any appropriate plastic material.

Each time the patient closes the mandibular molars on the maxillary molars, the pressure in the pad 24 is translated via the liquid into the reservoir 28. The reservoir may include, for example, a piston 30, which is biased by a spring 32, as shown in FIG. 3. With such an assembly, each time the corresponding mandibular molar closes on maxillary molar 22, the liquid in pad 24 is forced into reservoir 28 by way of tube 26 to move the piston 30 back against the pressure of spring 32. Then, when the mandibular molar is moved away from the maxillary molar, the spring returns the piston 30, forcing the liquid back into the pad 24, and exerting a pressure pulse against the molar 22. A similar pad may be positioned on molar 20, with its reservoir, if so desired.

The result of the action described above is to cause the headgear to provide an intermittent pulsation of pressure due to the natural masticating action of the lower jaw. As stated above, each pressure pulsation is delivered to the maxillary molar 22 when there is no occlusal pressure on it, and consequently is most effective for at that moment there is no resistance from the occlusion that would impede distalization of the maxillary molar. As also pointed out above, the vertical pressure from the occlusal pad also prevents the headgear from causing undesired extension of the maxillary molar.

It will be appreciated that although a particular embodiment of the invention has been shown and described, modifications may be made. It is intended in the following claims to cover all such modifications which come within the true spirit and scope of the invention.

What is claimed is:

1. An orthodontic appliance comprising: a bow element adapted to be engaged with a tooth of a patient to apply a pressure to the tooth to move the tooth in a predetermined direction; a liquid reservoir mounted on the bow element; a hollow resilient pad adapted to be mounted on the occlusal surface of a tooth of the patient; and a tubular member coupling the pad to the reservoir to carry liquid from the interior of the pad to the reservoir each time the patient bites to exert a compressive force on the pad so as to cause the bow to transmit a pulse of pressure to the first-named tooth each time the patient removes the compressive force from the pad.

2. The orthodontic appliance defined in claim 1, in which said bow element comprises the inner bow of a cervical extra oral headgear.

3. The orthodontic appliance defined in claim 2, in which said bow element is adapted to be engaged with a maxillary molar, and said pad is mounted on the occlusal surface of said molar.

4. The orthodontic appliance defined in claim 1, and which includes a spring-loaded piston mounted in said reservoir which transmits the pressure pulse to the bow.

* * * * *